United States Patent [19]

Russo

[11] Patent Number: 4,523,920

[45] Date of Patent: Jun. 18, 1985

[54] SURGICAL SUCTION DRAIN

[75] Inventor: Ronald D. Russo, Barrington, R.I.

[73] Assignee: SIL-FAB Corporation, Hudson, Mass.

[21] Appl. No.: 557,866

[22] Filed: Dec. 5, 1983

[51] Int. Cl.³ .......................................... A61M 27/00
[52] U.S. Cl. ...................................... 604/93; 604/280
[58] Field of Search ................. 604/92, 282, 280, 266, 604/43

[56] References Cited

U.S. PATENT DOCUMENTS

| | | | |
|---|---|---|---|
| 1,596,754 | 8/1926 | Moschelle | 604/282 |
| 2,134,152 | 10/1938 | Schwarzmayr | 604/93 |
| 3,630,206 | 12/1971 | Ginold | 604/102 |
| 3,860,008 | 1/1975 | Miner et al. | 604/93 |
| 3,957,054 | 5/1976 | McFarlane | 604/282 |
| 4,257,422 | 3/1981 | Duncan | 604/282 X |
| 4,398,910 | 8/1983 | Blake et al. | 604/93 |
| 4,445,897 | 5/1984 | Ekbladh et al. | 604/43 X |

FOREIGN PATENT DOCUMENTS

| | | | |
|---|---|---|---|
| 2233028 | 1/1975 | France | 604/93 |
| 2240026 | 3/1975 | France | 604/43 |
| 2248057 | 5/1975 | France | 604/43 |
| 105038 | 3/1917 | United Kingdom | 604/93 |

Primary Examiner—Stephen C. Pellegrino
Attorney, Agent, or Firm—Weingarten, Schurgin, Gagnebin & Hayes

[57] ABSTRACT

A surgical suction drain extruded from biologically inert medical grade silicone rubber includes first and second spaced flanges and a web integrally formed between and abutting the flanges defining first and second longitudinally extending and laterally directed exudate receiving channels. A longitudinally extending lumen is provided in the web that is directly connectable to a vacuum source. A plurality of transversely extending apertures are provided through the flanges each of which defines an exudate receiving passageway in communication with the central lumen, the exterior surfaces of both flanges, and with a corresponding one of the longitudinally extending and laterally directed channels. Tissue standoffs are provided on the flanges. An X-ray opaque strip is co-extruded on one of the flanges. Tabs are insert molded in the channels to provide structural strength for securing the drain to the body.

7 Claims, 5 Drawing Figures

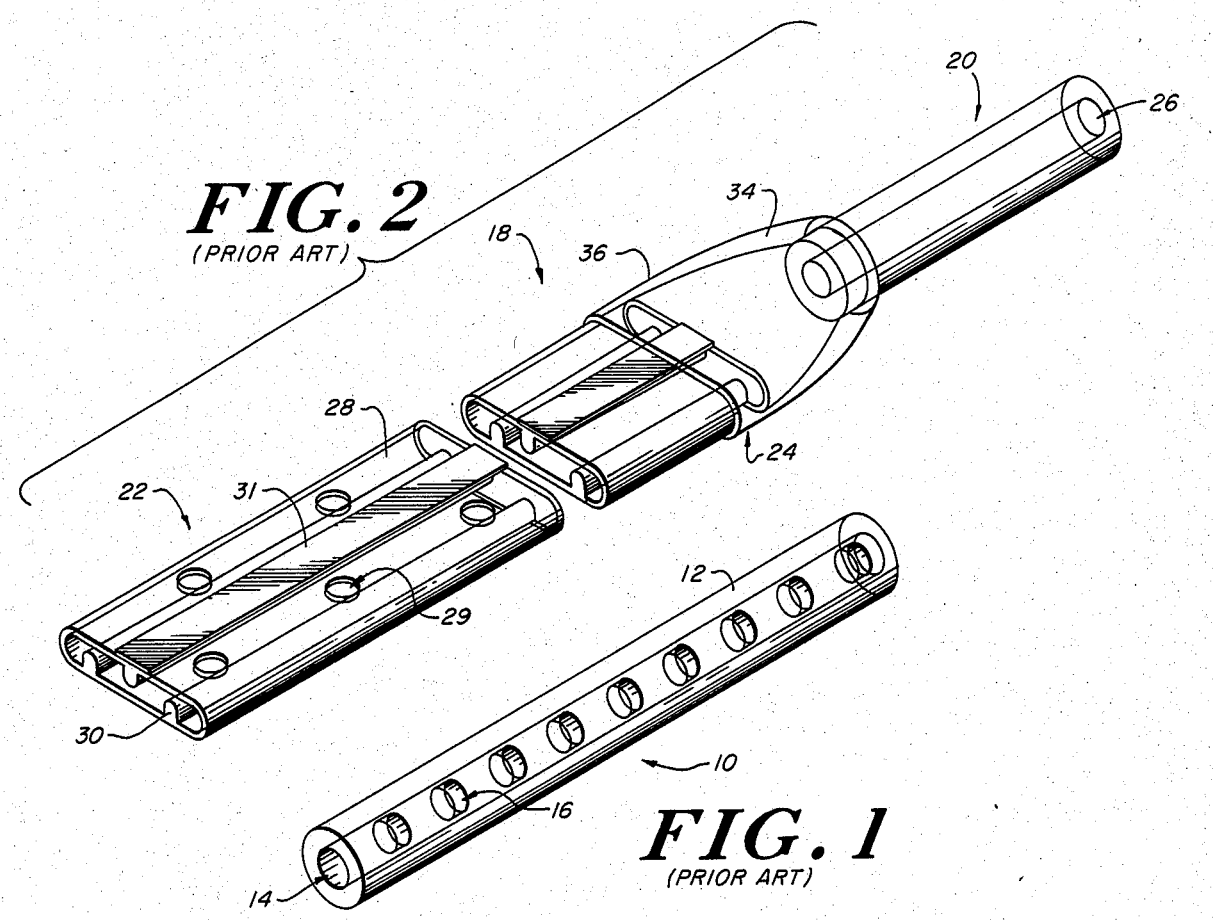
FIG. 2 (PRIOR ART)
FIG. 1 (PRIOR ART)
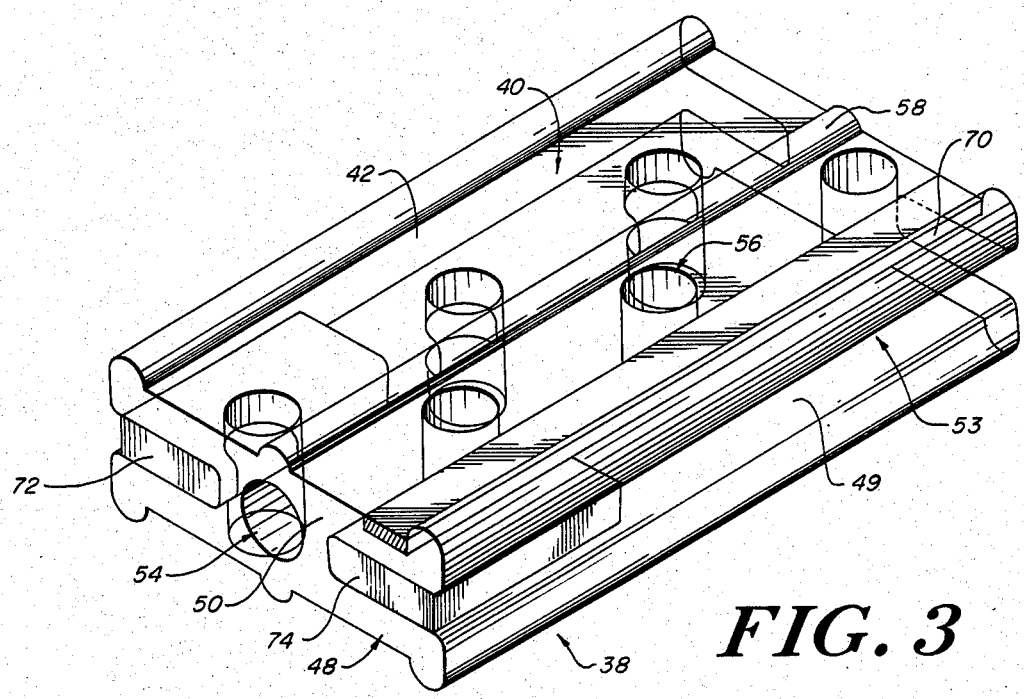
FIG. 3

SURGICAL SUCTION DRAIN

FIELD OF THE INVENTION

This invention is directed to the field of surgery, and more particularly, to a novel surgical suction drain.

BACKGROUND OF THE INVENTION

In many postoperative medical procedures, it is desirable to drain exudate from various body cavities to further the healing process. Typically, a tubular member is inserted into the body of a patient with its internal end in communication with the body cavity to be drained, and with its external end connected to a suction source. The negative pressure of the suction source draws the exudate from the cavity to be drained through the tube and exteriorly of the patient. Such devices are called upon to provide effective drainage; to prevent removal damage as a result of tissue to drain adhesion; to provide long term in situ drainage without patient discomfort or trauma; to readily conform to internal body contours without loss of drainage action; to be capable of expeditious and low-cost manufacture; to prevent inflammation of body tissue; and to prevent drain occlusion due to tissue being drawn into the drain. The heretofore known surgical drainage tubes are deficient of one or more of these aspects.

SUMMARY OF THE INVENTION

The novel surgical suction drain of the present invention includes first and second longitudinally extending and spaced apart flanges each having generally planar external and internal surfaces. A longitudinally extending web is integrally formed centrally between the flanges defining first and second longitudinally extending and laterally directed exudate receiving channels between the internal surfaces of the flanges and the web. A longitudinally extending lumen is provided through the web for connection to a controlled suction source. A plurality of transversely extending apertures are provided through the first and second flanges that are longitudinally spaced apart laterally alternately to either side of the longitudinally extending lumen. Each transversely extending aperture provides a passageway through which exudate can flow into the central lumen both from the generally planar external surfaces of the flanges and from a corresponding one of the longitudinally extending and laterally directed exudate receiving channels. A longitudinally extending rib is integrally formed centrally on each of the external planar surfaces of the flanges, and first and second longitudinally extending ribs are integrally formed laterally adjacent respective sides of each of the external planar surfaces of the flanges. The central ribs and laterally spaced ribs on each of the external surfaces of the flanges are co-operative to provide tissue standoffs for preventing occlusion of the transversely extending apertures. The surgical suction drain of the present invention is preferably integrally extruded from biologically inert medical grade silicone rubber. A longitudinally extending X-ray opaque strip may be co-extruded on the external surface of one of the flanges of the surgical drain to provide for X-ray observability of the drain when positioned in internal body cavities. A pad may be insert molded at pre-selected points along the surgical drain in corresponding longitudinally extending and laterally directed channels to provide structural strength for suturing and for providing a sealing surface at the point of entry of the surgical suction drain into a patient. The surgical suction drain of the present invention provides clogging-free, collapse-proof, and effective long-term drainage, and can be manufactured at comparatively low cost.

BRIEF DESCRIPTION OF THE DRAWINGS

Other features and advantages of the present invention will become apparent as the invention becomes better understood by referring to the following exemplary and non-limiting detailed description of the preferred embodiment, and to the drawings, wherein:

FIG. 1 is a perspective view illustrating a conventional surgical suction drain;

FIG. 2 is a perspective view illustrating another conventional surgical suction drain;

FIG. 3 is a perspective view illustrating a surgical suction drain according to the present invention;

DETAILED DESCRIPTION OF THE PREFERRED EMBODIMENT

Figure 4:
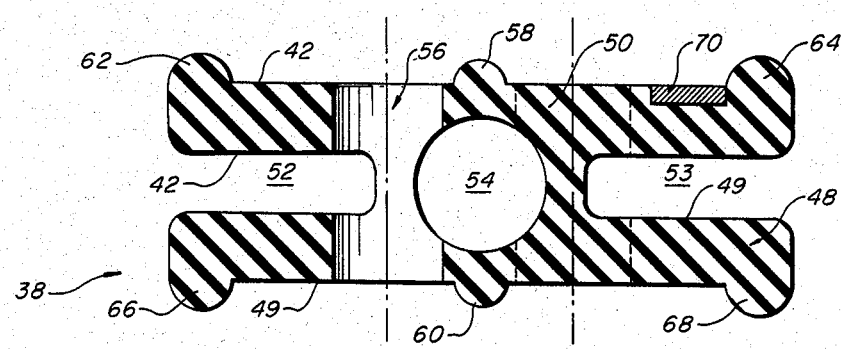
FIG. 4 is a sectional view illustrating the surgical suction drain according to the present invention.

Referring now to FIG. 1, generally designated at 10 is a conventional tubular surgical suction drain. Drain 10 includes a thick walled tube 12 having a longitudinally extending central aperture generally designated 14. A plurality of transverse apertures generally designated 16 are provided through the tube 12 that each communicate with the central aperture 14. In use, the tube 10 is inserted with one end into a body cavity and with its other end connected to a controlled source of negative pressure, not illustrated. Exudate in the body cavity is drawn through each of the apertures 16 into the central aperture 14 and exteriorly of the body cavity. The utility of the tubular surgical suction drain 10 is limited, among other things, however, due to patient discomfort induced by the thick walled tube; due to the difficulty in properly suturing the drain into position at the point of entry of the tube into the body of a patient; and due to occlusion of the passageways as a result of tissue being drawn thereinto by action of the negative pressure source.

Referring now to FIG. 2, generally designated at 18 is another conventional surgical suction drain. The surgical drain 18 includes a tubular portion generally designated 20 connectable to a controlled source of negative pressure, not shown, a flattened tubular portion generally designated 22 insertable into a body cavity to be drained, and a hub portion generally designated 24 connecting the flattened portion 22 to the tubular portion 20. The tubular portion 20 is generally of circular cross-section, and includes a central longitudinally extending aperture generally designated 26. The flattened tubular portion 22 includes a silicone rubber tube 28 having collapse-preventing staggered ribs 30 longitudinally formed along the interior surfaces thereof. A plurality of staggered apertures generally designated 29 are provided through the portion 22 defining exudate receiving passageways. An X-ray opaque strip 31 is provided along the external surface of the flattened tube 22 intermediate the staggered apertures 29. The hub 24 includes an end portion 34 adhesively fastened to the tubular portion 22 and an enlarged end portion 36 adhesively fastened to the flattened tubular portion 22. The utility of the drain 18 is limited, among other things, however, due to the costly and time consuming manual labor involved in adhesively joining the hub 24 to the flattened tubular portion 22 and to the circular tubular portion 20; due to rejects that must be discarded during manufacture as a result of improper molding and gluing; due to time consuming inspections and testing needed to insure that the adhesive provides a secure seal as well as not occluding the apertures as a result of glue leaks thereinto; and due to possible tissue occlusion of the staggered apertures as the tissue is drawn thereinto by the vacuum source.

Figure 5:
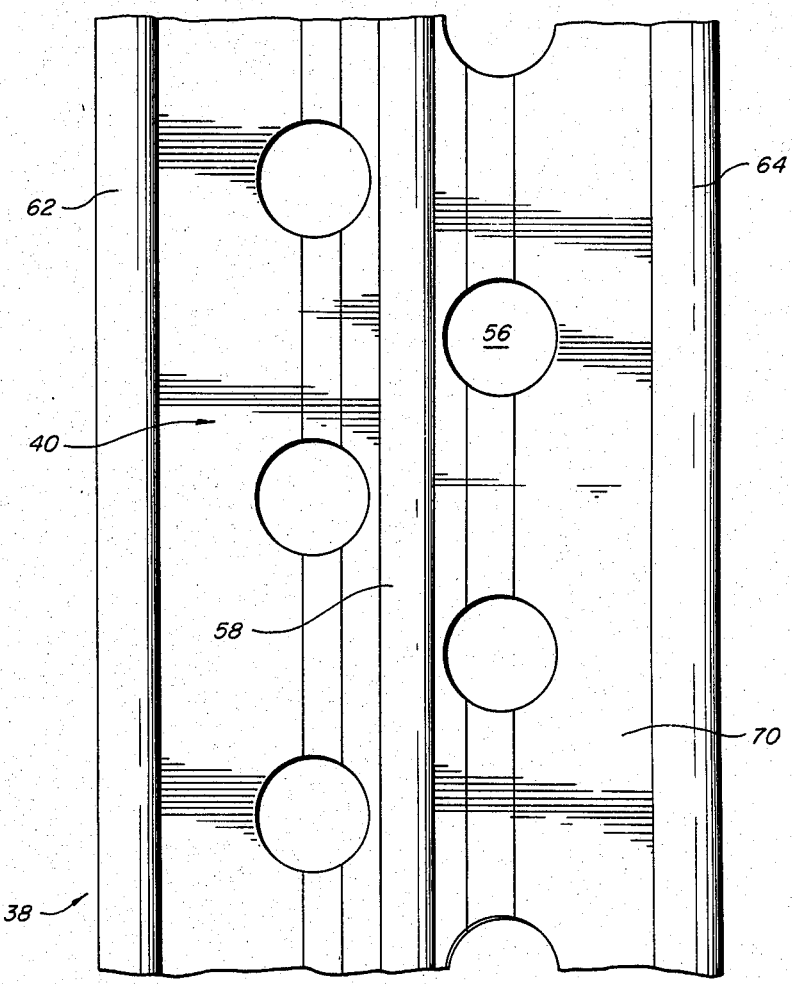
FIG. 5 is a plan view illustrating the surgical suction drain according to the present invention.

Referring now to FIGS. 3 through 5, generally designated at 38 is a novel surgical suction drain according to the present invention. The drain 38 is integrally extruded preferably of biologically inert medical grade silicone rubber. The drain 38 includes a first longitudinally extending flange generally designated 40 having generally parallel planar surfaces 42, a spaced apart and longitudinally extending second flange generally designated 48 having generally parallel planar surfaces 49, and a longitudinally extending web 50 integrally formed centrally between the flanges 40,48 defining first and second longitudinally extending and laterally directed exudate receiving channels generally designated 52,53 between confronting interior surfaces 42,49. The web 50 is provided with a longitudinally extending lumen generally designated 54 that is directly connectable to a controlled source of negative pressure, not shown.

A plurality of transversely extending apertures generally designated 56 are provided through the drain 38. The apertures 56 are preferably spaced apart longitudinally, with successive ones of the apertures 56 preferably alternating laterally to either side of the central lumen 54, although any other suitable spacing can be employed as well without departing from the inventive concept. Each of the apertures 56 has an open end in communication with corresponding external surfaces 42,49 of the flanges 40,48, and an interior opening in communication both with the central lumen 54 and with a corresponding one of the longitudinally extending and laterally directed exudate receiving channels 52,53. Exudate is thereby received both from the external surfaces 42,49 and from the sides of the drain 38 through the channels 52,53 into the lumen 54, wherefrom it is drawn exteriorly of the patient.

A longitudinally extending rib 58 is integrally formed centrally on the external surface 42 of the flange 40, and a longitudinally extending rib 60 is integrally formed centrally on the surface 49 of the flange 48. Longitudinally extending ribs 62,64 are integrally formed on the external surface 42 of the flange 40 laterally to each side thereof, and ribs 66,68 are integrally formed on the external surface 49 of the flange 48 laterally to each side thereof. The ribs 58,62,64 on the flange 40 and the ribs 60,66,68 on the flange 48 are co-operative to provide a tissue stand-off which prevents tissue from being drawn by the vacuum source into the transversely extending apertures 56 and thereby occluding the passageways.

An X-ray opaque strip 70 is provided on the external surface 42 of the flange 40. It provides X-ray observability of the surgical suction drain 38 when inserted in a body cavity. The strip 70 is preferably co-extruded with the surgical suction drain 38 and is recessed flush with the external surface 42.

Tabs 72,74 are provided in corresponding channels 52,53. The tabs 72,74 are preferably insert molded into the channels after extruded formation of the drain 38 to provide structural strength for suturing the drain to the patient and to provide a seal that prevents exudate leakage. The drain 38 is typically clear, and the tabs 72,74 are typically colored, for example, green or blue. The colored tabs 72,74 aid in locating the suture point and serve to initiate the proper positioning of the drain at the entry point into the body. The tabs may, for example, be 2 inches long and spaced apart longitudinally in the channels on 8 inch, 10 inch, or 16 inch centers.

It has been found that the surgical suction drain 38 provides effective long term in situ drainage, is substantially collapse-proof, substantially eliminates tissue clogging, provides long term and comfortable patient use, and can be manufactured at comparatively low cost.

It will be appreciated that many modifications of the presently disclosed invention are possible without departing from the scope of the appended claims.

What is claimed is:

1. A surgical suction drain, comprising:
    a first longitudinally extending flange having generally parallel planar external and internal surfaces;
    a second spaced apart longitudinally extending flange having generally parallel planar external and internal surfaces;
    a longitudinally extending web integrally formed centrally between and abutting the internal surfaces of said first and second flanges defining first and second longitudinally extending and laterally directed exudate receiving channels;
    said longitudinally extending web having a longitudinally extending lumen directly connectable to a controlled source of negative pressure; and
    said first and second flanges and said longitudinally extending web having a plurality of transversely extending and longitudinally spaced apertures therethrough each of which has open ends in communication with a corresponding one of said external surfaces of said flanges and an internal opening in communication both with a corresponding one of said first and second longitudinally extending and laterally directed exudate receiving channels and with said central lumen.

2. The invention of claim 1, further including first and second ribs integrally formed centrally on said external surfaces of respective ones of said first and second flanges to provide a tissue standoff.

3. The invention of claim 1, further including first and second ribs integrally formed laterally along the sides of each of said generally planar external surfaces of said first and second flanges to provide a tissue standoff.

4. The invention of claim 1, further including a X-ray opaque strip on one of said surfaces of one of said flanges.

5. The invention of claim 1, wherein said transversely extending apertures are spaced apart longitudinally laterally alternately to each side of said central lumen.

6. The invention of claim 1, wherein said drain is an elongated length of extruded biologically inert medical grade silicone rubber.

7. The invention of claim 6, further including first and second tabs co-extruded with said drain and selectively positioned in respective first and second exudate receiving channels to provide structural strength for suturing and to provide a seal preventing exudate leakage.

* * * * *